(12) United States Patent
Brown

(10) Patent No.: US 10,058,645 B2
(45) Date of Patent: Aug. 28, 2018

(54) SYSTEMS FOR ANTICOAGULATING BLOOD

(71) Applicant: Fenwal, Inc., Lake Zurich, IL (US)

(72) Inventor: Richard I. Brown, Northbrook, IL (US)

(73) Assignee: FENWAL, INC., Lake Zurich, IL (US)

( * ) Notice: Subject to any disclaimer, the term of this patent is extended or adjusted under 35 U.S.C. 154(b) by 80 days.

(21) Appl. No.: 15/430,730

(22) Filed: Feb. 13, 2017

(65) Prior Publication Data
US 2017/0157307 A1    Jun. 8, 2017

Related U.S. Application Data

(62) Division of application No. 12/861,974, filed on Aug. 24, 2010, now Pat. No. 9,603,989.

(51) Int. Cl.
A61M 1/00 (2006.01)
A61M 1/02 (2006.01)
A61M 1/36 (2006.01)

(52) U.S. Cl.
CPC ........ *A61M 1/0272* (2013.01); *A61M 1/3672* (2013.01); *H05K 999/99* (2013.01); *A61M 1/02* (2013.01); *A61M 1/3621* (2013.01); *A61M 2205/3334* (2013.01); *A61M 2205/52* (2013.01)

(58) Field of Classification Search
CPC ..... A61M 1/02; A61M 1/3621; A61M 1/3672
See application file for complete search history.

(56) References Cited

U.S. PATENT DOCUMENTS

| 4,094,461 A | 6/1978 | Kellogg et al. |
| 4,300,717 A | 11/1981 | Latham, Jr. |
| 4,385,630 A | 5/1983 | Gilcher |
| 4,425,114 A | 1/1984 | Schoendorfer |
| 4,526,515 A | 7/1985 | Devries |
| 4,551,131 A | 11/1985 | Miles |
| 4,769,001 A | 9/1988 | Prince |
| 4,806,247 A | 2/1989 | Schoendorfer |
| 5,423,738 A | 6/1995 | Robinson |
| 5,538,405 A | 7/1996 | Patno |
| 5,549,834 A | 8/1996 | Brown |

(Continued)

FOREIGN PATENT DOCUMENTS

WO    WO 96/39209     12/1996
WO    WO 9830275 A1   7/1998

OTHER PUBLICATIONS

International Search Report and Written Opinion for PCT Patent Application No. PCT/US2011/048721, dated Dec. 22, 2011.

(Continued)

Primary Examiner — Benjamin Klein
(74) Attorney, Agent, or Firm — Cook Alex Ltd.

(57) ABSTRACT

Systems are provided for anticoagulating blood. Whole blood is drawn from a donor into a system at a draw flow rate. Anticoagulant from an anticoagulant source is pumped into the system at an anticoagulant flow rate to mix with the blood. The anticoagulated blood may be subsequently processed in any of a number of known ways, including separating it and removing at least a portion of one of the components of the blood. Thereafter, at least a portion of the remaining blood may be returned to the donor. The anticoagulant flow rate is independent of the draw flow rate and can be based on a number of factors, including the weight of the donor and the rate at which the donor can metabolize the anticoagulant.

5 Claims, 1 Drawing Sheet

(56) References Cited

U.S. PATENT DOCUMENTS

| | | |
|---|---|---|
| 5,817,042 A | 10/1998 | Langley |
| 6,033,561 A | 3/2000 | Schoendorfer |
| 6,312,607 B1 | 11/2001 | Brown |
| 6,402,702 B1 | 6/2002 | Gilcher |
| 6,481,980 B1 | 11/2002 | Vandlik |
| 6,524,231 B1 | 2/2003 | Westberg |
| 6,855,120 B2 | 2/2005 | Grimm |
| 7,052,606 B2 | 5/2006 | Gibbs |
| 7,479,123 B2 | 1/2009 | Briggs |
| 7,601,298 B2 | 10/2009 | Waldo |
| 7,884,132 B2 | 2/2011 | Tolwani et al. |
| 2003/0062318 A1 | 4/2003 | Brown |
| 2005/0137517 A1 | 6/2005 | Blickhan |
| 2007/0110829 A1 | 5/2007 | Tolwani et al. |
| 2008/0299538 A1 | 12/2008 | Goodrich et al. |
| 2009/0215602 A1 | 8/2009 | Min |
| 2009/0221948 A1 | 9/2009 | Szamosfalvi et al. |

OTHER PUBLICATIONS

Extended European Search Report for Application No. EP 11820485 dated Feb. 15, 2018.

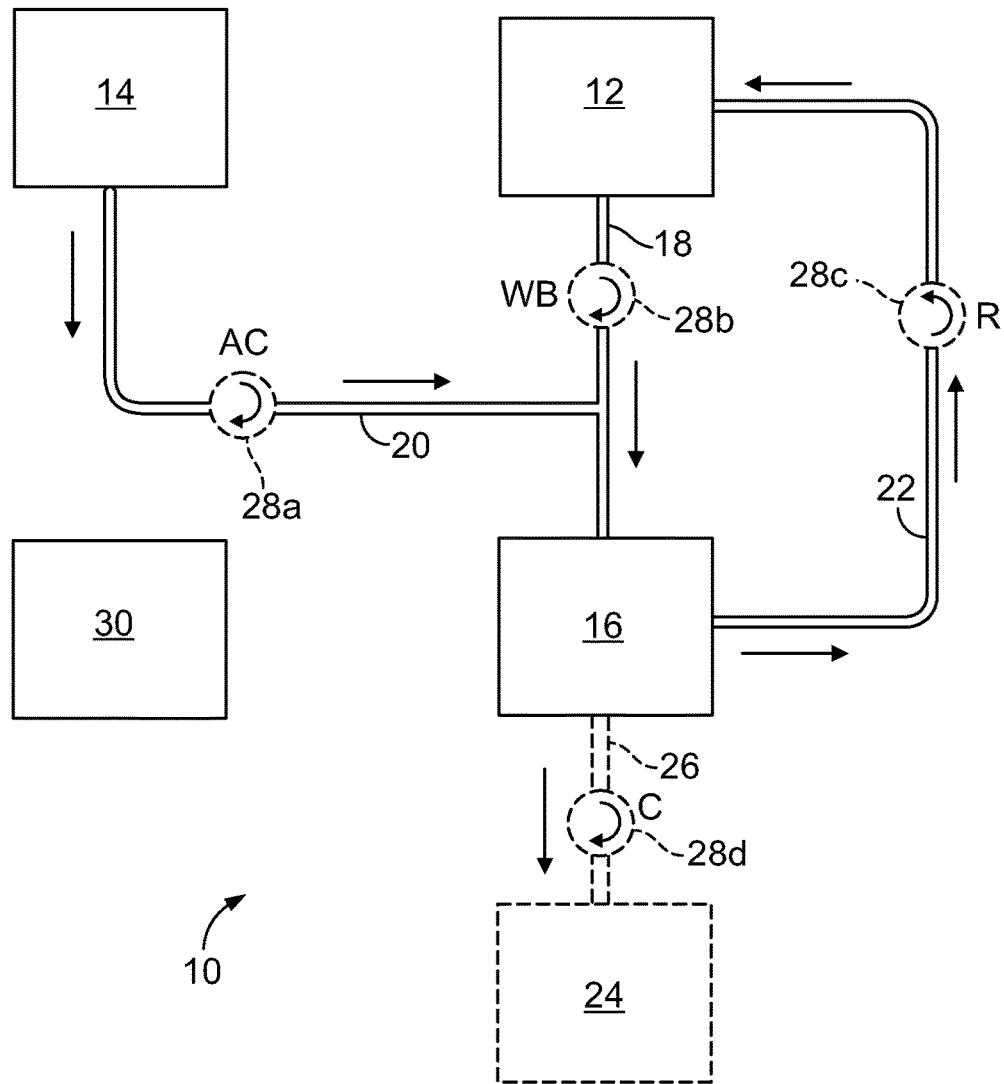

SYSTEMS FOR ANTICOAGULATING BLOOD

CROSS REFERENCE TO RELATED APPLICATIONS

This is a divisional of U.S. patent application Ser. No. 12/861,974, filed on Aug. 24, 2010, which is hereby incorporated herein by reference.

BACKGROUND

Field of the Disclosure

The present subject matter relates to systems and methods for blood or blood component processing which include the addition of an anticoagulant to the blood or blood component during a blood processing procedure.

Background

Whole blood and/or blood constituents may be processed in a wide variety of ways with different objectives and goals. For example, in apheresis whole blood is routinely separated into its various components, such as red blood cells, platelets, mononuclear cells and plasma. This is popularly used for the purpose of collecting one or more specific blood components for later administration to patients in need of those blood components, but may also be used for therapeutic purposes, for example, to remove or reduce the amount of a particular blood component from a patient as part of a medical treatment.

In typical apheresis systems, whole blood is drawn from a donor and combined with an amount of anticoagulant to retard coagulation during further processing. The anticoagulated blood is then processed through the system to obtain the needed separation. The blood components that are not stored for later use or removed for therapeutic purposes are typically returned to the donor or patient. These procedures may be carried out alone or in combination with other procedures or systems, such as pathogen removal or inactivation processes and/or devices for removing or inactivating certain pathogens that may accompany a blood component being collected or returned to the donor or patient.

Typical blood processing systems employ separate anticoagulant and whole blood pumps, which operate at a fixed ratio of whole blood flow rate to anticoagulant flow rate. As a result, the operation of the pumps is effectively constrained or tied together according to the predetermined ratio, and the anticoagulant pump rate is dependent upon and varies with the whole blood pump rate. Hence, if the rate of the whole blood pump is changed during a blood processing procedure (e.g., varying the rate between a relatively high level to a relatively low level and back), the anticoagulant pump flow rate will also be changed proportionally to maintain the predetermined ratio.

SUMMARY

In accordance with one aspect of the present disclosure, a system is provided for continuously anticoagulating blood. The system comprises a whole blood draw line, an anticoagulant flow line, and a controller. The whole blood draw line is adapted or configured for drawing whole blood from a donor. The anticoagulant flow line is adapted or configured for flowing anticoagulant from an anticoagulant source into the blood drawn from the donor. The controller is programmed to operate the system so as to draw blood from the donor at a draw flow rate and to add anticoagulant from the anticoagulant source into the drawn whole blood at an anticoagulant flow rate to form anticoagulated blood, with the anticoagulant flow rate being independent of the draw flow rate. The anticoagulant flow rate is calculated using the formula "AC=S*CIR*weight/concentration," where "AC" is the anticoagulant flow rate, "S" is a factor equal to the inverse of the percentage of anticoagulant to be returned to the donor, "CIR" is a citrate infusion rate at which the donor can metabolize the citrate, "weight" is the weight of the donor, and "concentration" is the citrate concentration of the anticoagulant.

As made clearer below, there are several aspects of the present subject matter which may be embodied separately or together in the methods and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

BRIEF DESCRIPTION OF THE DRAWINGS

The FIGURE is a diagrammatic view of an exemplary system and method for adding anticoagulant to whole blood and processing such anticoagulated blood.

DESCRIPTION OF THE ILLUSTRATED EMBODIMENTS

The embodiments disclosed herein are for the purpose of providing the required description of the present subject matter. They are only exemplary, and may be embodied in various forms and in various combinations. Therefore, specific details disclosed herein are not to be interpreted as limiting the subject matter as defined in the accompanying claims.

The FIGURE diagrammatically illustrates a blood processing system 10 which employs aspects of the present disclosure. Such a system will typically employ a disposable one-time use fluid processing assembly, module or circuit through which the fluids flow, and a durable reusable hardware module to which the disposable is mounted or otherwise cooperatively engaged to control the flow of fluids through the disposable module and the processing of the blood or blood components. Such systems are well known in the blood processing and blood banking fields, are commercially marketed by several companies and are described in a large number of patents, exemplary of which will be identified later and incorporated by reference herein.

The system 10, as shown for illustration only, comprises a vein access, generally at 12, an anticoagulant source 14, a blood processing assembly 16, a whole blood draw or flow path or line 18 for fluid flow from the vein access to the processing assembly, an anticoagulant fluid flow path or line 20 for fluid flow from the anticoagulant source to the whole blood draw line, a return flow path or line 22 for returning one or more blood components from the processing assembly 16 to the donor or patient via the vein access 12, and an optional collection flow path or line 26 for fluid flow connection between the processing assembly 16 and a container or reservoir 24. Fluid flow rates through the respective flow lines may be controlled by pumps 28a, 28b, 28c and 28d on the anticoagulant, whole blood, return and collection flow paths or lines, under the command of a central processor or controller 30, all as described in more detail below.

The above description of the system 10 is intended to be illustrative and not exhaustive. For example, the anticoagulant source 14 may be separate from the remainder of the system 10 and fluidly connected to the anticoagulant flow line 20 shortly before the donor is phlebotomized. Further, the anticoagulant flow line 20 may join the whole blood draw line 18 upstream, rather than downstream, of the pump 28b. Other system components, such as a source of saline priming fluid, leukocyte reduction filters, sensors and the like, although not illustrated in the FIGURE may be included in the system as desired.

Turning now to the various illustrated components, the vein access 12 may include, for example, a single vascular access member such as a phlebotomy needle, vascular catheter or other access device for use in single access-site (sometimes called "single-needle") procedures, in which whole blood is alternately drawn from a patient or donor and blood or blood components are alternately returned. The vein access also may include a pair of such access members for vascular access at different locations to permit simultaneous withdrawal of whole blood and return of blood or blood components.

The vein access 12 is fluid flow connected, such as by flexible plastic tubing, with a blood processing assembly 16 via a whole blood draw or flow line 18. It may be noted here that the fluid flow lines of the system 10 may have a variety of configurations and be made of any suitable material. For example, the flow lines may be provided as tubular conduits formed of either flexible tubing or the flow path may be preformed in a rigid plastic flow control cassette that is operated by solenoid, pneumatic or other valve arrangement to control flow direction through the cassette, as illustrated, for example in U.S. Pat. No. 5,538,405 to Patno et al. or U.S. Pat. No. 6,481,980 to Vandlik et al., both of which are incorporated by reference herein, or may be of any other suitable configuration.

The blood processing assembly 16 may be variously provided without departing from the scope of the present disclosure, and various devices may, for example, be used to obtain the treatment of blood and/or the separation of blood into its constituents, if desired. For example, the blood can be processed through a known centrifugal separation chamber, such as employed in the ALYX® or AMICUS® separators marketed by Fenwal, Inc. of Lake Zurich, Ill., which is an affiliate of Fresenius Kabi AG of Bad Homburg, Germany, or centrifugal blood separators made by other manufacturers including Fresenius Medical Care of Lexington, Mass.; Haemonetics Inc. of Braintree, Mass.; or CaridianBCT of Lakewood, Colo. Static or moving membrane type separators may also be used to remove a particular blood component or constituent. One example of such a separator is the Fenwal AUTOPHERESIS-C® separator, which processes the blood through an annular gap between an inner rotor and an outer housing, one or both of which mount membranes that allow a blood component to pass therethrough. The gap, blood flow rate and rotor speed are configured to generate couette flow, and specifically Taylor vortices, in the blood, which reduces membrane clogging and enhances filtration. More specifically, suitable blood processing assemblies 16 may include, but are not limited to, the centrifugal or spinning filtration membrane apheresis systems, such as those described in greater detail in U.S. Pat. No. 4,526,515 to DeVries; U.S. Pat. No. 5,194,145 to Schoendorfer; U.S. Pat. No. 6,312,607 to Brown et al.; U.S. Pat. No. 6,524,231 to Westberg et al.; U.S. Pat. No. 4,094,461 to Kellogg et al.; U.S. Pat. No. 7,052,606 to Gibbs et al.; U.S. Pat. No. 4,300,717 to Latham and U.S. Patent Application Publication No. 2009/0215602 to Min et al., all of which are hereby incorporated by reference.

As pointed out earlier, the blood processing assembly 16 does not necessarily require a blood separator and may include systems for other blood processing procedures, for example pathogen removal or inactivation, either alone or in combination with a separator or other blood processing devices, where all or a portion of the anticoagulated blood or blood products is return to the donor or patient. Pathogen activation has been proposed using a variety of inactivation agents or processes, such as exposure of blood or blood components to ultraviolet light of selected wavelengths before returning to the donor or administration to a patient. Also, it has been proposed to add an inactivation agent to whole blood or blood components, alone and in combination with light activation of the agent. Examples of pathogen inactivation systems that may be employed in the blood processing assembly 16 include systems such as the one described in greater detail in U.S. Pat. No. 7,601,298 to Waldo et al. or a blood processing system incorporating both a centrifuge and a light box for pathogen inactivation, such as the one described in greater detail in U.S. Pat. No. 7,479,123 to Briggs, both of which are incorporated herein by reference.

Depending on the nature of the blood processing assembly 16 and the ends desired for the blood processing procedure, the system 10 may optionally also include one or more collection receptacles 24 fluidly connected to an outlet of the blood processing assembly 16 via a collection flow line 26. In an apheresis procedure for collection of a desired or target blood constituent, for example, anticoagulated whole blood is flowed into the blood processing assembly 16 (e.g., a centrifuge), which separates the blood into two or more of its component parts. At least a portion of one of the components, such as platelets, red cells, mononuclear cells or plasma, or a combination of the foregoing, is collected in the collection receptacle 24 (e.g., a flexible container or bag), and the remainder of the separated blood (including a certain amount of anticoagulant) is returned to the donor via the return flow line 22. In other possible procedures where all of the processed blood is returned to the donor, there may not be a need for a collection receptacle 24.

For controlling the processing procedures, including the relative fluid flow rates, the system 10 further includes the controller 30, which is configured to control the operation of the system 10, particularly, the pumps 28a-28d and the operation of the blood processing assembly 16. The controller 30 may be provided as a computer or associated programmable microprocessor or other known means for controlling one or more of the elements of the system 10 in accordance with the procedure and steps set forth herein. Alternatively, a plurality of controllers may be employed rather than just a single controller 30. In either case, the controller may have programmed steps, flow rates and sequences, such as described later, for different desired procedures, so that the same hardware may be used with a variety of blood processing methods, with the same disposable fluid circuit or with fluid circuits that are unique to each procedure. For inputting or outputting data or information, the controller 30 may include additional elements, including a user interface such as a keyboard, touch screen, voice command module, or other means for entering commands without departing from the scope of the present disclosure.

The FIGURE shows a number of pumps 28a-28d associated with the various flow lines. The pumps 28a-28d are shown in broken lines because there will not typically be a pump associated with each flow line, but instead there typically will be one "floating" or "free flow" flow line that does not include a pump. For example, in one embodiment, the system 10 may include an anticoagulant pump 28a, a blood draw pump 28b, and a return pump 28c, with a collection pump 28d being omitted, thereby making the collection flow line 26 between the blood processing assembly 16 and the collection receptacle 24 the "floating" line. The flow rate of fluid through the "floating" line depends on the operational rates of the other pumps (in accordance with well-established fluid dynamic and conservation of mass principles), meaning that it can be passively controlled by adjusting the operational rates of the pumps. Any one of the pumps may be omitted, rendering the associated flow line the "floating" line. Accordingly, it will be appreciated that the draw flow rate WB (i.e., the rate at which whole blood is drawn into the system 10 from a donor) and the anticoagulant flow rate AC (i.e., the rate at which anticoagulant is added to the drawn whole blood) may be either actively controlled (if the associated flow line includes a pump) or passively controlled (if the associated flow line is the designated "floating" line). The draw flow rate WB and the anticoagulant flow rate AC are, however, preferably actively controlled by pumps 28b and 28a, respectively.

The pumps may be of any suitable construction or operate on any suitable principle. For example, one or more of the pumps may be a peristaltic pump, which operates by progressively compressing flow path tubing to move fluid therethrough. Peristaltic pumps are widely know in the apheresis and blood processing field. Alternatively, one or more of the pumps may be a diaphragm type pump that operates by alternately drawing fluid into and expelling it from a pump chamber. An example of such a pump chamber is found in the Fenwal ALYX® blood processing system, in which pump chambers are pre-formed into a rigid plastic cassette that also includes a flow path labyrinth. A flexible membrane overlies at least one side of the cassette and is operable under pneumatic-control, via the controller, with various portions of the membrane acting as a pump membrane in association with the pump chambers and other portions acting as flow control valves in association with the fluid flow paths. This arrangement is shown in greater detail in U.S. Pat. No. 6,524,231 to Westberg et al., incorporated by reference above. Other types of pumps may also be used that may be controlled by the controller 30 to control flow through the system.

The anticoagulant pump 28a (if provided) may be adapted for continuously adding anticoagulant from the anticoagulant source 14 to the drawn whole blood in the system 10 at an anticoagulant flow rate AC. The whole blood pump 28b (if provided) may be adapted for drawing whole blood from a donor at a draw flow rate WB. The return pump 28c (if provided) may be adapted for returning processed blood (or a portion thereof) to a donor at a return flow rate R. The collection pump 28d (if provided) may be adapted for collecting a separated blood component from the blood processing assembly 16 at a collection flow rate C. Alternatively, for whichever pump is omitted, the rate of fluid flow through the associated flow line (e.g., the anticoagulant flow rate AC if the anticoagulant pump 28a is omitted) may be controlled indirectly by the flow rates of the pumps, as noted above.

In use, the donor is phlebotomized using the vein access device 12. The controller 30 operates the whole blood pump 28b (if provided) to draw whole blood from the donor into the system 10 at the draw flow rate WB. If a whole blood pump 28b is not provided, then the controller 30 orchestrates the operation of one or more of the other pumps such that blood is drawn from the donor into the system at the draw flow rate WB. The controller 30 also operates the anticoagulant pump 28a (if provided) to continuously pump anticoagulant from the anticoagulant source 14 into the system 10 at the anticoagulant flow rate AC. If an anticoagulant pump 28a is not provided, then the controller 30 orchestrates the operation of one or more of the other pumps such that anticoagulant is added from the anticoagulant source 14 into the blood in the system 10 at the anticoagulant flow rate AC.

As pointed out above, in typical prior apheresis systems the whole blood and anticoagulant flow rates were controlled in accordance with a selected ratio of the whole blood blow rate to the anticoagulant flow rate (typically such ratio might be in the range of 7 to 11). This means that as the whole blood flow rate changes, the anticoagulant flow rate also changes, as they are interrelated and controlled by the selected ratio.

In accordance with features of this disclosure, unlike the prior systems referred to above, it is unnecessary for the draw flow rate WB and the anticoagulant flow rate AC of the blood processing system to be maintained at a predetermined or selected ratio. Instead, in methods and systems of the present disclosure, the rate at which anticoagulant is added to blood is independent of the rate at which the whole blood is drawn from a donor. Instead, the anticoagulant flow rate may be based on other factors and, if desired, be substantially uniform or constant so that within expected operational parameters it is independent of the whole blood flow rate.

One factor for the determination of an anticoagulant flow rate AC may be the rate at which the donor or patient can metabolize the anticoagulant or a component thereof. For example, the anticoagulant flow rate AC may be based, at least in part, upon the rate at which the donor or patient can metabolize a citrate constituent of the anticoagulant. Such a metabolic rate is referred to herein as the citrate infusion rate or CIR. The CIR of a particular person may not be known prior to the procedure, but may be predicted or estimated based on a variety of factors, including the person's weight. It has been found that, in general, humans can metabolize an anticoagulant containing a citrate at a rate approximately equal to 1.5 mgCitrate/kgDonor-weight/min. Acid-citrate-dextrose (referred to herein as "ACD"), a common anticoagulant in apheresis systems, contains approximately 21 mgCitrate/ml. Accordingly, as an example, applying the formula "AC=CIR*weight/concentration" (where "weight" is the weight of the patient or donor and "concentration" is the concentration of a constituent of the anticoagulant (e.g., a citrate) which is to metabolized by the donor), a donor weighing 150 pounds (approximately 68 kg) can tolerate and be expected to metabolize the amount of citrate received from about a 5 ml/min anticoagulant flow rate when the anticoagulant is ACD and, when using a worst case assumption, all the anticoagulant that flows into the blood is returned to the donor or patient, such as in an mononuclear cell collection (MNC) procedure, (1.5 mgCitrate/kgDonor-weight/min*68 kg/21 mgCitrate/ml=5 ml/min). Because an MNC procedure can operate with a whole blood to anticoagulant flow rate ratio as high as 15:1 without undue clotting, the whole blood withdrawal pump can operate as fast as 75 ml/min without returning more anticoagulant than the donor/patient can metabolize. Thus, a fixed anticoagulant flow rate of 5 ml/min can be used for any whole blood withdrawal rates up to about 75 ml/min, which is adequate as a high end of whole blood flow rates in an MNC procedure. In other procedures, different whole blood to anticoagulant flow rate ratios may be appropriate (e.g., a maximum ratio of 12:1 may be appropriate for a platelet collection procedure), but it will be understood that the above discussion is applicable regardless of the specific constraints associated with the procedure.

This may be adjusted depending on the donor's or patient's citrate tolerance. For donors known to be particularly sensitive to citrate (i.e., those requiring a lower CIR), the anticoagulant flow rate AC may be decreased to an appropriate level, with the resultant maximum whole blood draw rate also reduced. Similarly, for donors known to tolerate a higher CIR (e.g., a CIR approximately equal to 2 mgCitrate/kgDonor-weight/min), the anticoagulant flow rate AC may be increased to a higher acceptable level, with the resultant maximum whole blood draw rate also increased. As the weight and metabolism of the donor will not significantly change during a blood processing procedure, the anticoagulant flow rate may remain substantially constant or uniform during the procedure.

Another factor in selecting an appropriate anticoagulant flow rate AC may be the nature of the blood processing procedure. This factor is referred to herein as "S" and has the effect of varying the initial calculation of the anticoagulant flow rate AC based upon the percentage of anticoagulant that will actually be returned to the donor during a blood processing procedure. For example, in mononuclear cell ("MNC") collection procedures or pathogen inactivation procedures, it is expected that nearly all of the anticoagulant added to the blood will eventually be returned to the donor, rather than being collected as a harvested blood component. In such procedures, with approximately a 100% anticoagulant return rate, S=1 and the fixed anticoagulant flow rate AC will be equal to the donor's weight multiplied by the donor's CIR and divided by the citrate concentration of the anticoagulant (e.g., 5 ml/min, as calculated above for an apheresis procedure employing ACD as an anticoagulant for a donor weighing 150 pounds with a CIR of 1.5 mgCitrate/kgDonor-weight/min).

Alternatively, there may be a blood processing procedure in which less than all of the anticoagulant will be returned to the donor. Typically, the anticoagulant mixes substantially uniformly with the plasma constituent of blood, meaning that apheresis procedures for separating and collecting plasma will also have the effect of removing a quantity of anticoagulant from the system prior to return to the donor. For example, if half of the plasma (and, hence, half of the anticoagulant) is estimated or calculated to be separated and removed from the system during an apheresis procedure, the anticoagulant flow rate may be doubled because only half of the anticoagulant will be returned and metabolized by the donor. Thus, for a 50% plasma/anticoagulant removal apheresis procedure employing ACD as an anticoagulant for a donor weighing 150 pounds with a CIR of 1.5 mgCitrate/kgDonor-weight/min, S=2 and the anticoagulant flow rate may be approximately 10 ml/min. An anticoagulant flow rate twice that of what is appropriate for the exemplary MNC procedure is appropriate for the plasma collection procedure because only half of the anticoagulant is ultimately returned to and metabolized by the donor. In this way, it will be seen that the anticoagulant flow rate may be based at least in part on the nature of the blood processing procedure.

To generalize the above factors and their relationship to the fixed anticoagulant flow rate, the following formula applies:

"AC=S*CIR*weight/concentration," where "AC" is the fixed anticoagulant flow rate, "S" is the inverse of the percentage of anticoagulant to be returned to the donor (which may be predicted or measured or estimated or calculated), "CIR" is the donor's citrate infusion rate (which may be predicted or measured or estimated or calculated), "weight" is the weight of the donor, and "concentration" is the concentration of a constituent of the anticoagulant (e.g., a citrate) in the anticoagulant which is to be metabolized by the donor.

Hence, the anticoagulant flow rate AC is essentially independent of the draw flow rate WB and is instead based on factors including the weight and CIR of the donor and the percentage of anticoagulant which will be returned to the donor from the blood processing assembly 16. The draw flow rate WB and the anticoagulant flow rate AC may vary independently of each other, although the anticoagulant flow rate AC will typically remain substantially constant during the blood processing procedure.

To the extent that there is any correlation between the whole blood draw flow rate WB and the anticoagulant flow rate AC, the ratio therebetween may be monitored by the controller 30 to ensure that it does not exceed a particular level. For example, MNC procedures may be run with a whole blood to anticoagulant ratio as high as about 15:1, so the draw flow rate WB may be varied (e.g., to keep a problematic vein open) up to a level 15 times that of the anticoagulant flow rate AC. If the anticoagulant flow rate AC is to remain uniform at approximately 5 ml/min during an exemplary MNC procedure, the whole blood pump may be operated at any rate (and varied independently of the anticoagulant flow rate AC) up to a maximum draw flow rate of approximately 75 ml/min. It will be appreciated that the ability to modify the whole blood draw flow rate WB without necessarily modifying the anticoagulant flow rate AC will result in the ratio of whole blood to anticoagulant flow potentially varying and has a number of advantages, such as decreased computer and controller calculations and commands and monitoring.

Returning now to the exemplary blood processing procedure, the anticoagulated blood passes into the blood processing assembly 16, which processes the blood (e.g., by inactivating pathogens contained therein and/or separating out a target component or components of the blood and optionally passing it/them to the collection receptacle 24). At least a portion (and potentially all in some procedures) of the processed anticoagulated blood is passed out of the blood processing assembly 16, through the return flow line 22 and returned to the donor via the vein access device 12. The fluid returned to the donor may contain an amount of anticoagulant, but the fixed anticoagulant flow rate AC (according to the present disclosure) is such that the donor is able to metabolize the anticoagulant and the whole blood flow may be varied as described above without any needed change to the anticoagulant flow rate.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A system for continuously anticoagulating blood comprising:

a whole blood draw line through which whole blood is drawn from a donor;

an anticoagulant flow line through which anticoagulant containing a citrate from an anticoagulant source is flowed into the whole blood drawn from the donor; and a controller programmed to operate the system so as to draw blood from the donor at a draw flow rate, and operate the system so as to add anticoagulant from the anticoagulant source into the whole blood drawn from the donor at an anticoagulant flow rate to form anticoagulated blood, wherein the anticoagulant flow rate is independent of the draw flow rate and is calculated using the formula "AC=S*CIR*weight/concentration," where "AC" is the anticoagulant flow rate, "S" is a factor based on the percentage of anticoagulant predicted to be returned to the donor, "CIR" is a citrate infusion rate at which the donor can metabolize said citrate, "weight" is the weight of the donor, and "concentration" is the citrate concentration of the anticoagulant.

2. The system of claim 1, wherein the anticoagulant flow rate is substantially constant.

3. The system of claim 1, wherein the controller is further programmed to operate the system to return at least a portion of the anticoagulated blood to the donor.

4. The system of claim 1, further comprising a blood processing assembly adapted to process at least a portion of the anticoagulated blood, wherein the anticoagulant flow rate is based at least in part on the nature of the processing to be applied to said at least a portion of the anticoagulated blood.

5. The system of claim 1, further comprising a blood processing assembly adapted to inactivate one or more pathogens contained within the whole blood drawn from the donor.

* * * * *